United States Patent
Curtis, Jr. et al.

(10) Patent No.: US 6,249,119 B1
(45) Date of Patent: Jun. 19, 2001

(54) ROTATING ELECTROMAGNETIC FIELD DEFECT DETECTION SYSTEM FOR TUBULAR GOODS

(75) Inventors: William W. Curtis, Jr.; Roy C. Grubbs, both of Houston, TX (US)

(73) Assignee: ICO, Inc., Houston, TX (US)

(*) Notice: Subject to any disclaimer, the term of this patent is extended or adjusted under 35 U.S.C. 154(b) by 0 days.

(21) Appl. No.: 09/413,416

(22) Filed: Oct. 6, 1999

Related U.S. Application Data

(60) Provisional application No. 60/103,411, filed on Oct. 7, 1998.

(51) Int. Cl.[7] .............................. G01N 27/82; G01R 33/12
(52) U.S. Cl. .......................... 324/242; 324/227; 324/229; 324/232; 324/233
(58) Field of Search ..................................... 324/220, 221, 324/227, 229, 232, 233, 239–243

(56) References Cited

U.S. PATENT DOCUMENTS

| | | | |
|---|---|---|---|
| 2,065,119 | * 12/1936 | Davis, Jr. ........................ 324/240 X |
| 2,124,579 | * 7/1938 | Knerr et al. ..................... 324/242 X |
| 2,467,306 | * 4/1949 | Habig ................................. 324/242 |
| 4,263,551 | * 4/1981 | Gregory et al. .................... 324/233 |
| 4,629,985 | * 12/1986 | Papadimitriou et al. ............ 324/232 |
| 4,818,935 | * 4/1989 | Takahashi et al. ............... 324/242 X |
| 4,954,777 | * 9/1990 | Klopfer et al. ...................... 324/232 |

* cited by examiner

Primary Examiner—Gerard R. Strecker
(74) Attorney, Agent, or Firm—Jenkens & Gilchrist, a Professional Corporation

(57) ABSTRACT

The defect detection system of the present invention includes an encircling coil for providing a saturating DC magnetic fields to tubular goods. Also included is an encircling drive coil for applying a low level AC field using three-phase AC. Encircling pick up coils within the AC drive coils detect uniform, time varying magnetic fields to reveal defects within the tubular goods passing through the system.

7 Claims, 2 Drawing Sheets

ROTATING ELECTROMAGNETIC FIELD DEFECT DETECTION SYSTEM FOR TUBULAR GOODS

This application claims the benefit of U.S. Provisional Patent Application No. 60/103,411 filed Oct. 7, 1998.

FIELD

The present invention relates to non-destructive testing; more particularly, the present invention relates to non-destructive testing using electromagnetic inspection techniques of tubular goods made from ferromagnetic materials.

BACKGROUND

For many years there has been a need to inspect the tubular goods inserted into wells for defects. Such defects may manifest themselves as reductions or variations in the cross sectional area of the tubing walls, pitting, or longitudinal defects (sometimes called rod wear). Because of the long, slender shape of a section of tubular goods, it is extremely difficult to visually inspect the inside surface of tubular goods. Accordingly, the prior art evidences various non-destructive inspection techniques. Such non-destructive inspection techniques include the use of electromagnetic flux. One example of a system which uses electromagnetic inspection techniques to inspect tubular goods is described in U.S. Pat. Nos. 4,710,712; 4,492,115; 4,636,727; 4,704,580; and 4,792,756.

SUMMARY

The non-destructive defect detection system for the electromagnetic inspection of tubular goods of the present invention is based on the use of time varying electromagnetic fields. The time varying electromagnetic fields used in the instant invention include Eddy current techniques, and AC flux leakage methods. These Eddy current techniques and AC flux leakage methods are used in combination with a saturating DC electromagnetic field to overcome the effects of the permeability changes found in tubular goods made from ferromagnetic materials. Specifically, three-phase AC in the outer driven coils produces signals representative of defects in a plurality of inner pick-up coils. Since the disclosed inspection system for ferromagnetic tubular goods is based on the use of time varying electromagnetic fields, the methods used in the present invention are inherently independent of the travel speed of the tubular goods through the defect detection system and do not require the use of integrator or derivative circuitry.

DESCRIPTION OF THE DRAWING FIGURES

A better understanding of the Defect Detection System for Tubular Goods of the present invention may be had by reference to the drawing figures wherein.

DESCRIPTION OF THE EMBODIMENTS

To obtain accurate results in the non-destructive electromagnetic inspection of tubular goods made from ferromagnetic materials, it is necessary to overcome the permeability changes found in the non-magnetized ferromagnetic materials. This overcoming of permeability changes is accomplished by the use of an outer encircling coil 20 which applies a saturating DC magnetic field to the tubular goods 100 being inspected for defects. This outer encircling coil 20 is of a solenoid design and has sufficient length long enough to assure that the area of the tubular goods 100 being inspected for defects is within a uniform saturated DC magnetic field. Further, the outer encircling coil 20 which provides the uniform saturated DC magnetic field is driven by a constant current. If needed, this constant current may be regulated to prevent changes in the saturated DC magnetic field level for improving the quality of the signals received and thus the overall quality of the inspection results or defect detections.

Figure 1A:
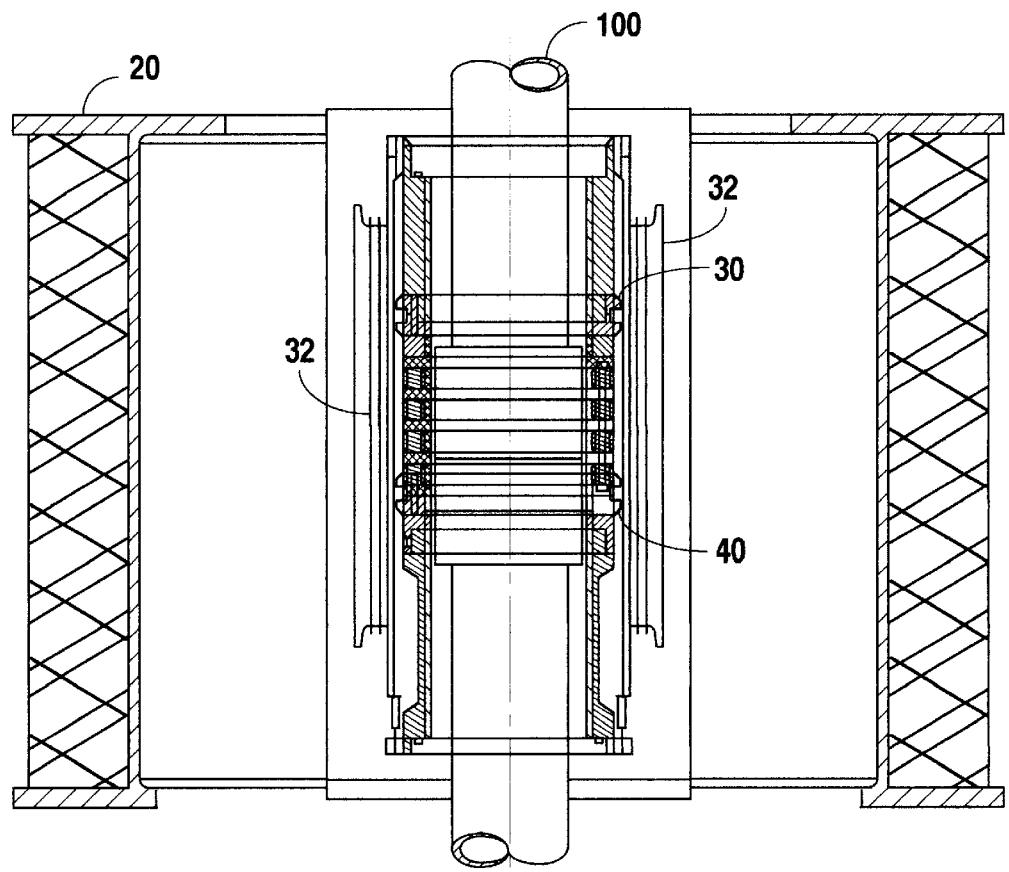
FIG. 1A is a schematic elevational view in partial section showing the arrangement of the coils used in the defect detection system.
Figure 1B:
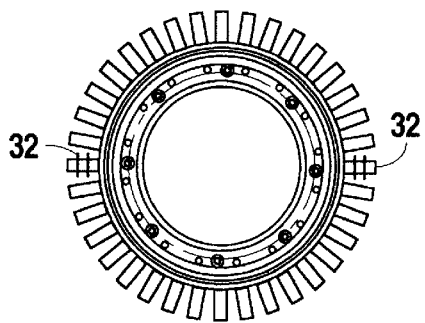
FIG. 1B is a bottom view of the outer driven coil portion of FIG. 1A.
Figure 1C:
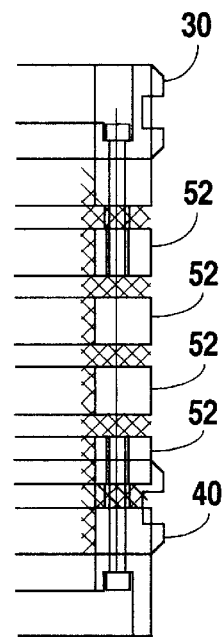
FIG. 1C is an enlarged view of a portion of the pickup coils as shown in FIG. 1A.

A key part of the electromagnetic inspection of tubular goods 100 is to determine variations in the cross-sectional area (CSA) of the substantially cylindrical solid portion of the tubular goods 100. As shown in FIG. 1A and FIG. 1C, CSA may be determined by use of an encircling drive 30 coil to apply a low level AC electromagnetic field to the tubular goods 100. The low level AC electromagnetic field is used in combination with at least one encircling pick up coil 40 spaced away from the drive coil 30 to receive signals representative of the CSA of the tubular goods 100 being inspected. The CSA measurement of the tubular goods being inspected is based on the AC coupling of the encircling drive coil 30 which applies a low level AC field and at least one encircling pick up coil 40. The output signal from the encircling pickup coil 40 is then processed by looking at both its phase and its amplitude. The phase and amplitude of the signal are then used to determine variations in the cross-sectional area of the tubular goods being inspected by techniques well known to those of ordinary skill in the art.

Where it is required to determine rod wear or pitting within the tubular goods 100, multiple AC drive coils 32 (three phase) are used. These AC drive coils 32 are shown in FIGS. 1A and 1B. While the windings of only two AC drive coils 32 are shown in FIG. 1B, one of ordinary skill in the art will understand that the AC drive coils 32 surround the tubular goods 100 being inspected These multiple AC drive coils 32 are wound in a manner to be driven by several (the same number as the number of AC drive coils) sine waves to create a uniform, time varying electromagnetic field that moves and rotates around the circumference of the tubular goods 100 being inspected. The windings of these multiple AC drive coils 32 are wound to be innerwoven flat coils. As previously indicated, these innerwoven flat coils are configured to surround the outside of the tubular goods 100. Further, these innerwoven flat coils are spaced away from the outer surface of the tubular goods 100 being inspected. These innerwoven flat coils resemble the field coils typically found in a three phase motor. The application of three-phase AC in the electromagnetic inspection method of the instant invention using these innerwoven flat coils is analogous to the method used in three-phase motors to create the rotating magnetic field that makes the armature turn in a three-phase motor.

Figure 1D:
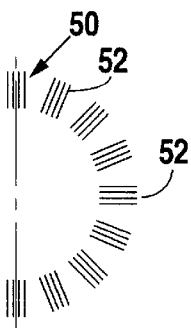
FIG. 1D is a schematic view of the top of one side of the encircling pick-up coil assembly.
Figure 1E:
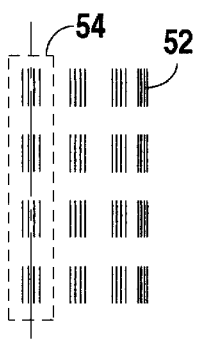
FIG. 1E is a schematic view of one side of the encircling pick-up coil assembly.

Multiple arrays 54 of groups of individual pick up coils 52 as shown in FIG. 1C, FIG. 1D and FIG. 1E having a substantially rectangular cross-section, and the same number of turns of wire, are placed both end to end and parallel to the long axis of the tubular goods 100 being inspected. These multiple arrays 54 of groups of individual pick up coils 52 are then used to monitor the uniform, time varying electromagnetic field in the outer AC drive coils 32. The multiple arrays 54 of groups of individual rectangular pick up coils 52 are evenly spaced around the circumference of the tubular goods 100 as shown in FIG. 1D. Each group of individual pick up coils 52 has a cross-section of about 0.5 inches in length and about 0.4 inches in width. The pick up coils are oriented perpendicular to the tubular goods 100 and the AC drive coils 32. In the preferred embodiment, the number of groups of individual pick up coils 52 per array 54 which are positioned around the pickup assembly 50 (FIG. 1D) which surrounds the circumference of the tubular goods 100 was chosen to be sixteen, as this is the number of groups of individual pick up coils 52 that matches the available channels in commercial multiplexers and sixteen arrays also provide adequate electromagnetic coverage for a quality inspection of the tubular goods 100 for defects.

The signals obtained by the groups of individual coils 52 within each array 54 of rectangular pick up coils 52 are combined by a digital signal processing computer and then processed by the computer using digital fast fourier transforms resident in the computer. The detection of pitting is enhanced by using the difference of the signals obtained from the non-adjacent individual coils 52 within a particular array 54 of pick up coils. The detection of rod wear is enhanced by summing the signals from the groups of individual coils 52 within a particular array 54 of pick up coils. The summed signals are analyzed by using digital fast fourier transforms, looking at both phase and amplitude information, to detect and grade both pitting and rod wear defects. The signals provided by the pick up coil arrays 54 may alternatively be used to determine changes in the cross-sectional area of the tubular goods.

Figure 2:
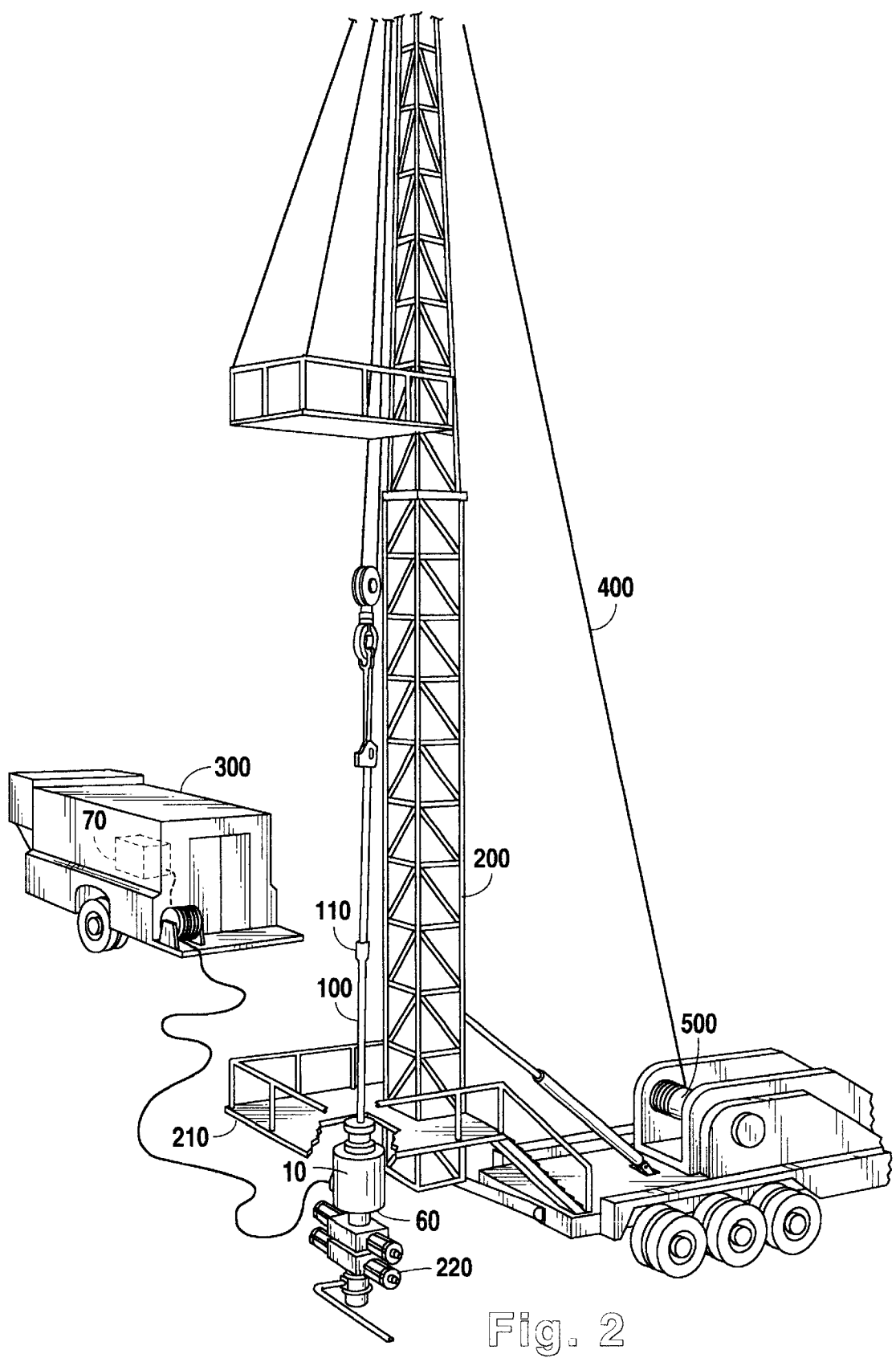
FIG. 2 is a perspective view of a typical well rig including the defect detection system of present invention.

As shown in FIG. 2, the defect detection system 10 of the present invention may be contained in a housing 60 and located below the floor 210 of the rig 200 and above the blow-out preventers 220. The tubing 100 passes through the defect detection system 10 as shown in FIG. 1A. Signals from the defect detection system 10 are conveyed to a digital signal processor 70.

Counting the joints 110 in strings of tubular goods 100 made up from individual discrete tubular sections is accomplished by using outside diameter measurements obtained from commercially available sensors (not shown). These commercially available sensors are designed to measure the distance between the face of the sensor and the outside diameter surface of the tubular goods 100. Since the coupling portions or joints 110 between the various individual discrete sections of tubular goods 100 typically have a larger diameter than the body of the individual discrete sections of tubular goods 100—a reliable method to track joint count by sensing larger outside diameters is provided by these commercially available sensors. Multiple pairs of such sensors may be used. When such multiple pairs of sensors are used, tubing ovality measurements may be added to the inspection process. It has been found that tubing ovality measurements are particularly important if the inspection system of the present invention is used to inspect coil tubing.

The system for recording the number of joints 110 may also be used to determine if the axial location of the tubular goods 100 within the inspection equipment is off center. Such information regarding the exact axial location of the tubular goods 100 within the signal processing equipment 300 is used to electronically compensate signal processing for the off-center location of the tubular goods 100 and, if needed, alert the operator to the off-center travel of the tubular goods 100 through the defect detection system 10.

Tracking the location of the defects in individual discrete section of tubular goods 100 used with a drilling or production rig 200 in relation to the location of various couplings 110 between the individual discrete sections of tubular goods 100 is performed by correlating the movement of the tubular goods 100 to the movement of the fast-line 400 on a pulling rig 500 in oil field applications. This is done by one of the two following methods:

a. Using a fast-line monitor system with a built-in quadrature encoder that tracks the travel of the fast-line 400. This assembly is suspended from the rig with straps to track the travel of the fast-line 400. Because the fast-line 400 is connected to the tubing string 100, there is a direct correlation between fast-line 400 travel and tubing string 100 travel.

b. Using a fast-line monitor assembly with a built-in quadrature encoder. This fast-line monitor assembly mounts adjacent to the drum of the pulling rig 500. Distance is measured as the fast line comes off the drum of the pulling rig 500. This method for tracking the location of the individual discrete tubing string 100 sections, and accordingly the location of defects in relation to the couplings 110, has the advantage of reducing physical injury risks to the people working near the tubular goods 100 since there is no need to climb on the rig 200 to install this type of fast-line 400 travel monitoring assembly.

Alternatively, the defect detection system 10 of the present invention described above may be located above the slips or between the slips and the blowout preventers 200, as shown in FIG. 2, if the defect detection system 10 is used to inspect tubular goods 100 used on a production or drilling rig 200.

While the present invention has been described by reference to its preferred embodiment, those of ordinary skill in the art will understand that still other embodiments are enabled by the foregoing disclosure. Such other embodiments shall be included within the scope and meaning of the appended claims.

What is claimed is:

1. A defect detection system for use in finding defects on the internal surface of tubular goods, said defect detection system comprising:

an outer encircling coil surrounding the tubular goods being inspected for defects, said outer encircling coil constructed and arranged to apply a saturating DC magnetic field;

a plurality of AC drive coils surrounding the tubular goods being inspected for defects and within said outer encircling coil, said plurality of AC drive coils constructed and arranged to apply a uniform, low level, time varying AC field using three-phase AC;

said plurality of AC drive coils being further constructed and arranged to be driven by sine waves for the creation of said uniform, time varying electromagnetic field that rotates around the circumference of the tubular goods being inspected;

multiple arrays of rectangular pick up coils within said AC drive coils, where each array includes a plurality of sets of rectangular pickup coils, said multiple arrays of rectangular pick up coils being evenly spaced around the tubular goods being inspected for defects and oriented in a flat plane radial to the tubular goods and said sets of rectangular pickup coils being axially spaced along the length of said tubular goods, said multiple arrays of rectangular pick up coils constructed and arranged to monitor said uniform, low level, time varying AC field;

a digital signal processing computer using digital fast Fourier transforms constructed and arranged to analyze phase and amplitude signals received from said multiple arrays of rectangular pick-up coils to detect pitting defects and rod wear defects on the internal surface of the tubular goods being inspected.

2. The defect detection system as defined in claim 1 wherein the current flow to the outer encircling coil constructed and arranged to apply a saturating DC magnetic field is regulated.

3. The defect detection system as defined in claim 1 wherein said plurality of AC drive coils are innerwoven flat coils.

4. The defect detection system as defined in claim 1 wherein each individual coil in said multiple arrays of rectangular pick up coils has the same number of turns of wire.

5. The defect detection system as defined in claim 1 further including means for recording a joint count when the tubular goods being inspected include joints connecting multiple sections of pipe or tubing.

6. The defect detection system as defined in claim 1 wherein the location of the defects is tracked in relation to the couplings joining the sections of tubular goods.

7. The defect detection system as defined in claim 1 further including an encircling drive coil for applying a low level AC electromagnetic field to the tubular goods:

at least one encircling pick up coil spaced apart from said encircling drive coil; and whereby variations in the cross-sectional area of the tubular goods may be determined by analyzing the phase and amplitude of the signal received by said at least one encircling pick up coil.

* * * * *